United States Patent [19]

Duffett

[11] Patent Number: Plant 5,620

[45] Date of Patent: Dec. 31, 1985

[54] CHRYSANTHEMUM PLANT NAMED SPEARS

[75] Inventor: William E. Duffett, Salinas, Calif.

[73] Assignee: Yoder Brothers, Inc., Barberton, Ohio

[21] Appl. No.: 574,722

[22] Filed: Jan. 27, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Spears particularly characterized as to uniqueness by the combined characteristics of spoon capitulum form; daisy capitulum type; white ray floret color; diameter across face of capitulum ranging from 7 to 8 cm. at maturity; uniform eight week photoperiodic flowring response to short days; medium plant height when grown as a pinched spray pot mum; spreading branching pattern; tolerance of both low 13° C. and high 24° C. night, 38° C. day temperatures for initiation of buds and development of flowers.

3 Drawing Figures

1

The present invention comprises a new and distinct cultivar of *Chrysanthemum morifolium,* Ramat., named Spears.

Spears is a product of a planned breeding program which had the objective of creating new chrysanthemum cultivars for pinched spray pot mum programs having daisy capitulum type, white floret color, eight week flowering response and the ability to produce commercially acceptable quality in year round programs. Such traits in combination were not present or required improvement in previously available commercial cultivars.

Spears was originated from a cross made in a controlled breeding program in Salinas, Calif. in 1978. The female parent was Quills, disclosed by U.S. Plant Pat. No. 4,401, originated in part by the present inventor from a hybridization of two unnamed seedlings. The male parent of Spears was an unnamed seedling identified as 78200003, originated from a cross between two unnamed seedlings.

Spears was discovered and selected as one flowering plant within the progeny of the stated cross by William E. Duffett in June 1980 in a controlled environment in Salinas, Calif.

The first act of asexual reproduction of Spears was accomplished when vegetative cuttings were taken from the initial selection in August 1980 in a controlled environment in Salinas, Calif. by a technician working under formulations established and supervised by William E. Duffett. Horticultural examination of selected units initiated Feb. 17, 1982 has demonstrated that the combination of characteristics as herein disclosed for Spears are firmly fixed and are retained through successive generations of asexual reproduction.

Spears has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Spears

2 which in combination distinguish this chrysanthemum as a new and distinct cultivar:

(1) Spoon capitulum form.

(2) Daisy capitulum type.

(3) White ray floret color.

(4) Diameter across face of capitulum ranging from 7 to 8 cm. at maturity.

(5) Uniform eight week photoperiodic flowering response to short days.

(6) Medium plant height (requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots).

(7) Spreading branching pattern.

(8) Tolerance of low 13° C. temperature.

(9) Tolerance of high 24° C. night and 38° C. day temperature.

The accompanying photographic drawings depict typical leaf and inflorescence characteristics of Spears. Sheet 1 is a color photograph of a plant of Spears grown as a pinched spray pot mum, with colors being as accurate as possible with renditions of this type. Sheet 2 is a black and white photograph of three views of the inflorescence of Spears. Sheet 3 shows the leaves of Spears in three stages of growth (mature, intermediate, immature).

Of the many commercial cultivars known to the present inventor, the most similar in comparison to Spears is Quills, disclosed in U.S. Plant Pat. No. 4,401. Reference is made to attached Chart A which compares certain characteristics of Spears to those same characteristics of Quills.

Spears develops a more spreading, branching pattern, shorter plant height, smaller capitulum diameter, slower flowering response period and more abundant pollen. The ray florets of Spears have shorter tubes and longer flattened areas. The two varieties are similar in color, form, type and temperature tolerance for bud initiation and flower development.

In the following description, color references are made to The Royal Horticultural Society Colour Chart. The color values were determined between 9:00 A.M. and 9.15 A.M. on Dec. 1, 1983 under 150 foot-candle light intensity at Salinas, Calif.

Classification:

*Botanical.*—*Chrysanthemum morifolium,* Ramat., cv Spears.

*Commercial.*—Spoon daisy spray pot mum.

I. Inflorescence:

A. *Capitulum.*—Form: Spoon. Type: Daisy. Diameter across face: 7 to 8 cm.

B. *Corolla of ray florets.*—Color (General tonality from a distance of three meters): White. Color (abaxial): 155D to 155B. Color (adaxial): 155D. Shape: Tubular base. Open and flat from mid section to tip.

C. *Corolla of disc florets.*—Color (mature): 7B including pollen. Color (immature): 145A-B.

D. *Reproductive organs.*—Androecium; Present disc florets only; abundant pollen. Gynoecium: Present both ray and disc florets.

II. Plant:

A. *General appearance.*—Height: Medium. Branching pattern: Spreading.

B. *Foliage.*—Color (abaxial): 137A. Color (adaxial): 147B. Shape: Deeply lobed, coarsely serrated.

CHART A
COMPARISON OF SPEARS AND QUILLS

| CULTIVAR | RAY FLORET COLOR | CAPITULUM FORM AND TYPE | BRANCHING PATTERN | DIAMETER ACROSS FACE OF CAPITULUM |
|---|---|---|---|---|
| SPEARS | WHITE | SPOON DAISY | SPREADING | 7 to 8 cm. |
| QUILLS | WHITE | SPOON DAISY | SEMI-UPRIGHT | 6.5 to 10 cm. |

-continued

CHART A
COMPARISON OF SPEARS AND QUILLS

| CULTIVAR | PLANT HEIGHT | FLOWERING RESPONSE PERIOD | TEMPERATURE TOLERANCE | POLLEN |
|---|---|---|---|---|
| SPEARS | MEDIUM 25 to 35 cm. | 8 WEEK | 13° C. 24°, 38° C. UNIFORM | ABUNDANT |
| QUILLS | MEDIUM 30 to 40 cm. | 7 WEEK | 13° C. 24°, 38° C. UNIFORM | SPARSE |

COMPARISONS MADE OF PLANTS GROWN AS PINCHED SPRAY POT MUMS SALINAS, CALIFORNIA AND LEAMINGTON, ONTARIO, CANADA

I claim:

1. A new and distinct cultivar of *Chrysanthemum morifolium,* Ramat., plant named Spears, as described and illustrated, particularly characterized as to uniqueness by the combined characteristics of spoon capitulum form; daisy capitulum type; white ray floret color; diameter across face of capitulum ranging from 6 to 8 cm. at maturity; uniform eight week flowering response; medium plant height; spreading branching pattern; tolerance of both low 13° C. and high 24° C. night, 38° C. day temperatures for initiation of buds and development of flowers.

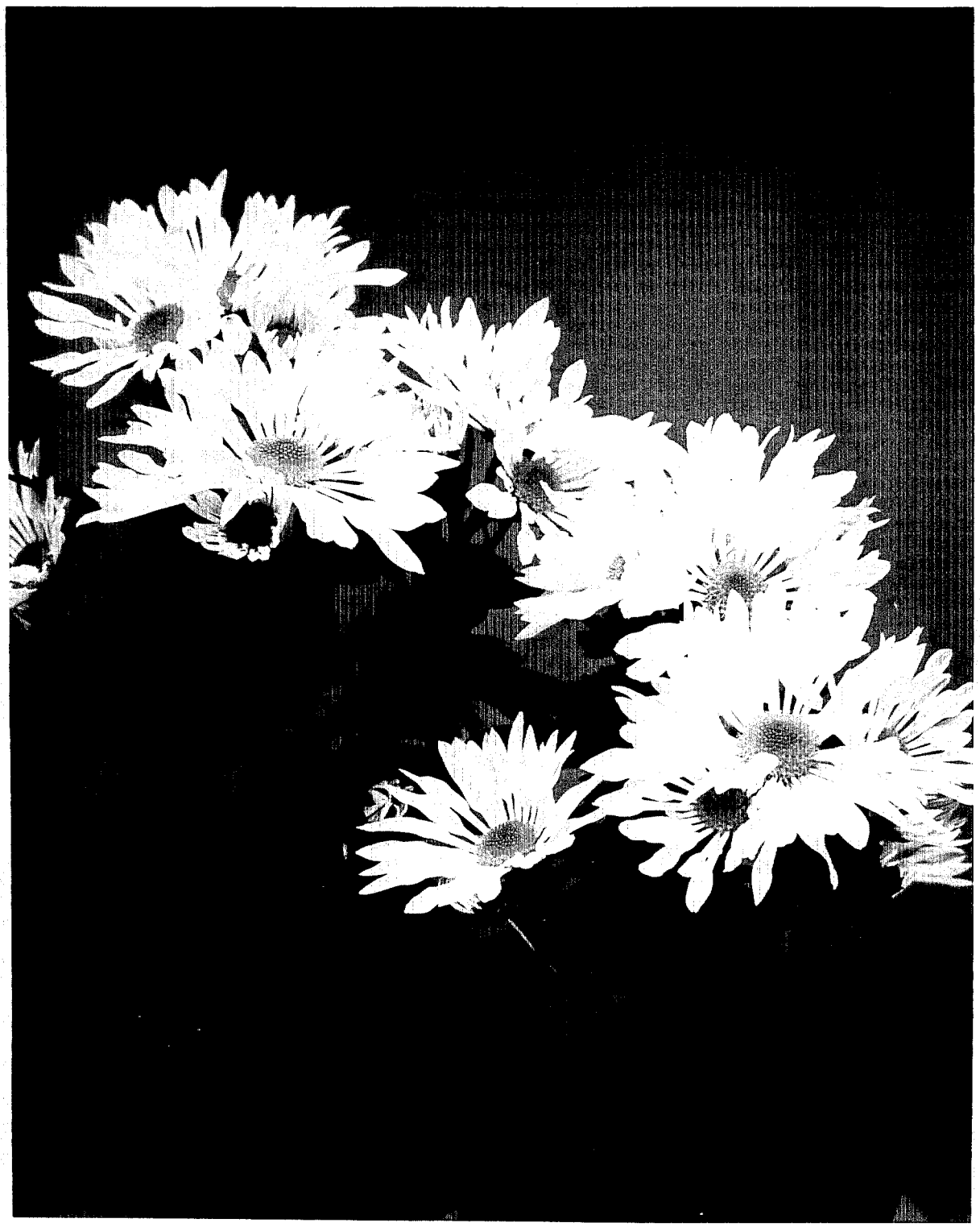

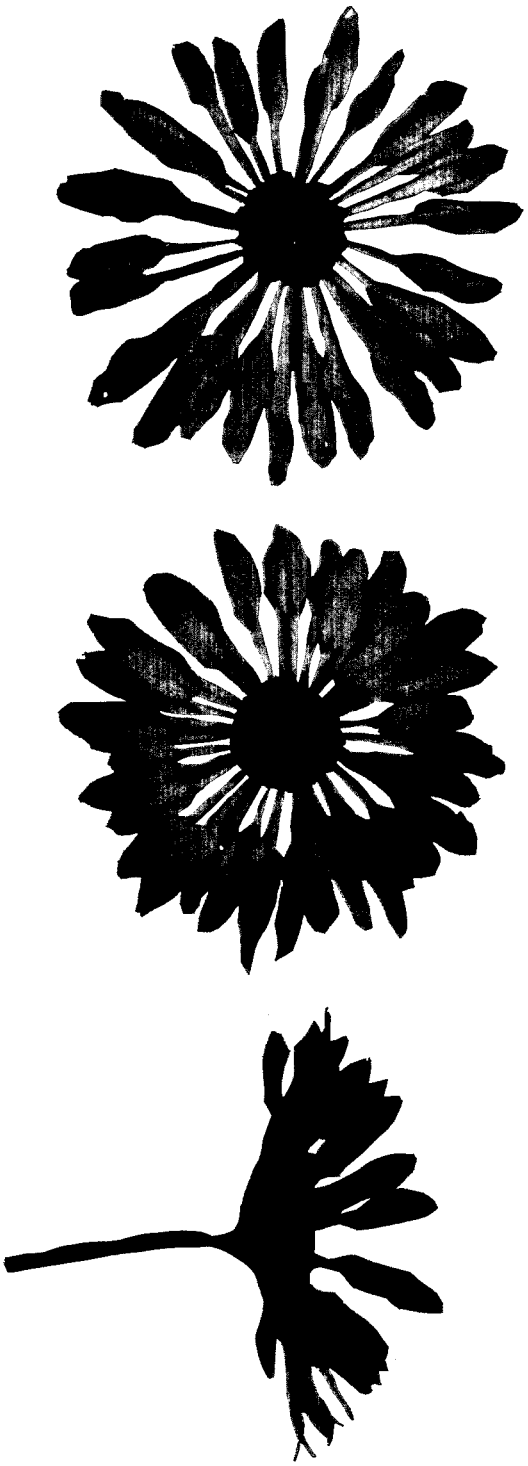

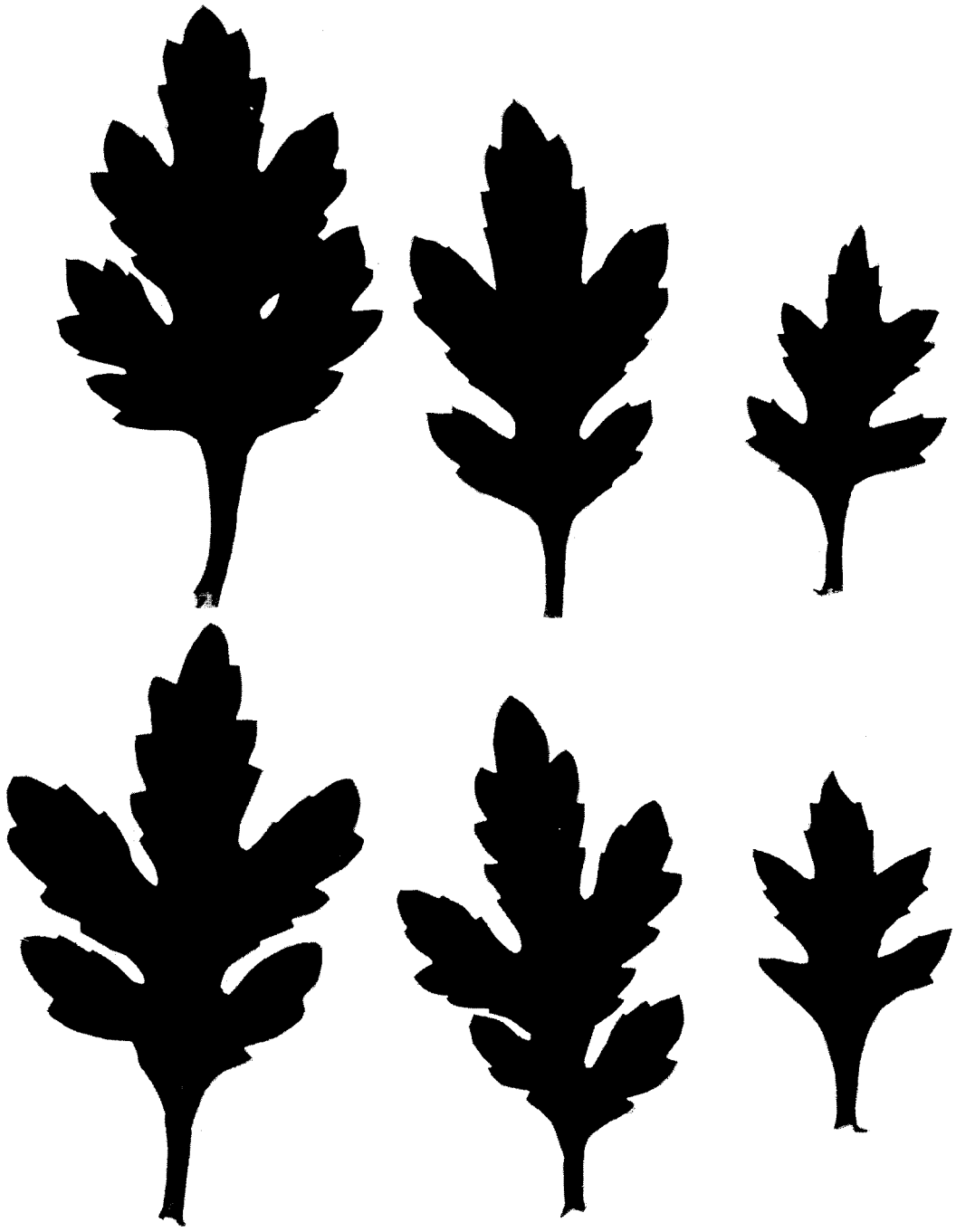

* * * * *